United States Patent [19]

Sturm et al.

[11] 4,278,613

[45] Jul. 14, 1981

[54] SULFUR-CONTAINING OXIME COMPOUNDS, PROCESSES FOR PRODUCING THEM, AND THEIR USE FOR PROTECTING CULTIVATED PLANTS

[75] Inventors: Elmar Sturm, Aesch; Heinrich Schempp, Arlesheim; Henry Martin, Allschwil, all of Switzerland

[73] Assignee: Ciba-Geigy Corporation, Ardsley, N.Y.

[21] Appl. No.: 68,123

[22] Filed: Aug. 20, 1979

[30] Foreign Application Priority Data

Aug. 28, 1978 [CH] Switzerland .......................... 9081/78

[51] Int. Cl.³ ............................................ C07C 121/52
[52] U.S. Cl. .................................. 260/465 D; 71/103; 71/90; 71/88; 260/347.5; 549/71; 560/165
[58] Field of Search ..................................... 260/465 D

[56] References Cited

U.S. PATENT DOCUMENTS

| 3,483,246 | 12/1969 | Kaufman | 260/465 |
|---|---|---|---|
| 4,070,389 | 1/1978 | Martin | 260/465 E |

FOREIGN PATENT DOCUMENTS 1141487  12/1968  Fed. Rep. of Germany .

*Primary Examiner*—Catherine L. Mills
*Attorney, Agent, or Firm*—Frederick H. Rabin

[57] ABSTRACT

Sulfur-containing oxime compounds of the formula I given herein are suitable for protecting cultivated plants against the phytotoxic action of aggressive agricultural chemicals, particularly herbicides. There are described methods for producing sulfur-containing oxime compounds of this type, and examples are given illustrating the application of these compounds.

6 Claims, No Drawings

SULFUR-CONTAINING OXIME COMPOUNDS, PROCESSES FOR PRODUCING THEM, AND THEIR USE FOR PROTECTING CULTIVATED PLANTS

The present invention relates to sulfur-containing oxime compounds corresponding to the formula I, to their production, to compositions containing such oxime compounds as active ingredients, and to the application of compositions of this type for protecting cultivated plants against the action of aggresive agricultural chemicals, particularly herbicides.

The active ingredients usable for the said purpose correspond to the following general formula I $$Ar\text{-}SO_n\text{---}\underset{\underset{N\text{---}O\text{---}Q}{\|}}{C}\text{---}X$$

wherein
n is 0, 1 or 2,
Ar
(a) is a phenyl group

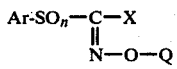

(b) is a naphthyl group substituted by $R_2$ and $R_3$,
(c) is a 5- to 10-membered heterocyclic radical which contains a maximum of 3 identical or different hetero atoms N, O and/or S, and which is substituted by $R_2$, $R_3$ and $R_4$, and which can be substituted by oxo or thiono, or wherein, if n is 0,
Ar
(d) is a radical R—CO—, wherein
R is a radical —$OR_5$, in which $R_5$ is an aliphatic group having a maximum of 8 C atoms, or an araliphatic group having a maximum of 15 C atoms, or a cycloaliphatic or aromatic group each having a maximum of 10 C atoms, with possible substituents of the aromatic radicals or of the cycloaliphatic radical being halogen, —CN, —$NO_2$, lower alkyl, lower alkoxy or halogenoalkyl, or R is a radical —NH—CO—NH—$R_7$, or a radical —N($R_6$)($R_7$), wherein $R_6$ is hydrogen or lower alkyl, and $R_7$ is hydrogen or an aliphatic group having a maximum of 8 C atoms, or an araliphatic group having a maximum of 15 C atoms, or a cycloaliphatic or aromatic group each having a maximum of 10 C atoms, with possible substituents of the aromatic groups or of the cycloaliphatic radical being halogen, —CN, $NO_2$, lower alkyl, lower alkoxy or halogenoalkyl, or R is a radical —N($R_6$)($R_7$), wherein $R_6$ and $R_7$ together form a 5- or 6-membered heterocyclic ring, which can contain oxygen as a further possible hetero atom, $R_1$ is hydrogen, halogen, lower alkyl, lower alkoxy, or a phenoxy group which is in the para position and which can be unsubstituted or substituted a maximum of twice by halogen, CN, $NO_2$ or $CF_3$, $R_2$, $R_3$ and $R_4$ independently of one another are each hydrogen, halogen, CN, $NO_2$, lower alkyl, lower alkoxy, halogenoalkyl, halogenoalkoxy, lower alkanoyl, OH, phenyl, halogenophenyl, lower carbalkoxy, lower alkoxycarbonyl, lower alkoxycarbonyloxy, lower carbamoyloxy, lower alkylthio, lower alkylsulfonyl, phenalkoxy, cyclohexyl, $NH_2$, —NH-lower alkyl, —N(-lower alkyl)$_2$, lower alkanoylamino, carboxylic acid amide or sulfonic acid amide, X is hydrogen, —CN, halogen, lower alkyl, lower alkanoyl, —COOH, a carboxylic acid ester group or a carboxylic acid amide group, Q is hydrogen, lower alkyl which can be interrupted by hetero atoms, or can be substituted by halogen or cyano, or Q is lower alkenyl or halogenoalkenyl, lower alkynyl, $C_3$-$C_7$-cycloalkyl which is unsubstituted or substituted by halogen, or Q is a lower alkanecarboxylic acid ester group, a lower alkanecarboxylic acid thioester group, a lower alkanecarboxylic amide group, an aliphatic acyl group, an araliphatic or cycloaliphatic acyl group, or an unsubstituted or substituted aromatic or heterocyclic acyl group, or Q is an alkylsulfonyl group, a sulfonic acid amide group, a metal salt, a quaternised ammonium salt, an aliphatic, araliphatic or cycloaliphatic carbonic acid, thiocarbonic acid or carbamoyl group, or an unsubstituted or substituted aromatic or heterocyclic carbonic acid, thiocarbonic acid or carbamoyl group.

By halogen in the formula I is meant fluorine, chlorine, bromine or iodine.

Carboxylic acid esters and thioesters are carboxylic acid lower alkyl esters and carboxylic acid lower alkyl thioesters. Acyl groups in this connection are carboxylic acid groups. Carboxylic acid amides denote, besides —$CONH_2$, also monoalkyl-substituted or symmetrically or unsymmetrically dialkyl-substituted amides, wherein the alkyl groups are lower alkyl.

The term 'alkyl' on its own or as part of a substituent embraces branched-chain or straight-chain $C_1$-to $C_8$-alkyl groups; 'lower alkyl' on its own or as part of a substituent denotes $C_1$-$C_4$-alkyl. Examples are: methyl, ethyl, propyl, isopropyl, butyl, isobutyl, sec-butyl and tert-butyl, as well as the higher homologues: amyl, isoamyl, hexyl, heptyl and octyl together with their isomers. Accordingly, alkanoyls or cyanoalkyls contain an additional C atom. Lower alkenyl or alkynyl groups correspondingly contain a maximum of 4 C atoms.

The term 'aliphatic group' includes saturated (alkyls) and also unsaturated (alkenyls, alkadienyls, alkynyls), halogen-substituted or cyano-substituted radicals, and such radicals interrupted by oxygen, all of which contain a maximum of 8 carbon atoms.

The term 'aromatic group' embraces phenyl and naphthyl.

An araliphatic radical includes an unsubstituted or mono- to tri-substituted phenyl or naphthyl group, which is attached by way of lower alkyl or lower alkenyl to the radical of the molecule. Examples are the base substances benzyl, phenethyl and phenylallyl and also homologues.

The term 'heterocyclic acyl group' embraces 5- or 6-membered heterocyclic carboxyl compounds having a ring hetero atom from the series N, O and S. Examples which may be mentioned are the radicals of furancarboxylic acid, thiophenecarboxylic acid, nicotinic acid, isonictinic acid and others. Cycloalkyl groups are cyclopropyl, cyclobutyl, cyclopentyl, cyclohexyl and cycloheptyl. Cycloaliphatic radicals correspond to these ring systems, but can contain in addition, depending on the possibility, one or more double bonds.

Possible metal salts in this connection are cations of the I to IV groups of the periodic system and also heavy metal salts. Examples are Na, K, Ca, Mg, Al, Zn, Cu, Fe, Mn, Co and Ni.

Quaternary ammonium salts contain as identical or different substituents: hydrogen, $C_1$–$C_{12}$-alkyl, lower hydroxyalkyl, benzyl, amino, di-lower alkylamino, or they form from two valencies and the N atom a 5- or 6-membered heterocyclic ring having optionally a further hetero atom N, O or S.

The partially novel compounds of the formula I are oxime ethers, oxime esters, oxime carbamates and oxime (thio)carbonates.

The invention relates also to the novel compounds of the formula I, with the exception of those prior known compounds wherein X is $=$CN and at the same time Q is hydrogen or methyl, Ar is a 4-substituted phenyl group (with the substituents hydrogen, fluorine, chlorine and $C_1$–$C_3$-alkyl), and n is the number 2. These compounds are prior known from the German Auslegeschrift No. 1,141,487 as fungicides. An antidote effect has not so far been described.

The oximes of the formula I are excellently suitable for protecting cultivated plants, such as cultivated millet, rice, maize, varieties of cereals (wheat, rye, barley and oats), cotton, sugar beet, sugar cane, soybean, and so forth, from being attacked by agricultural chemicals harmful to plants, particularly by herbicides of the most varied classes of substances, such as triazines, phenylurea derivatives, carbamates, thiolcarbamates, halogenoacetanilides, halogenophenoxyacetic acid esters, subst. phenoxyphenoxyacetic acid esters and -propionic acid esters, subst. pyridineoxyphenoxy-acetic acid esters and -propionic acid esters, benzoic acid derivatives, and so forth, in cases where these do not act selectively or not sufficiently selectively, that is to say, where they damage the cultivated plants in addition to the weeds to be controlled. The invention relates both to the compositions containing these oxime ethers of the formula I together with herbicides, and to compositions containing these oxime ethers of the formula I as the sole active ingredient. Plant protection products which contain an antidote of the formula I (also known as a 'safener') can be produced, marketed and used without concomitantly containing the herbicide (or some other aggressive agricultural chemical) of which the harmful effects on cultivated plants are to be reduced. An important possibility of application is seed dressing, which is undertaken at a point of time quite independent of the time of application of the agricultural chemicals (for example herbicide). A further field of application is the treatment of a soil in which there are still present residues of a herbicide used during the previous cultivation season, which residues could harm the new crop of cultivated plants to be sown.

The antidote property is a substance property which is independent of the cultivated plant and of the agricultural chemical of which the action is to be selectively weakened, and which is inherent in a preparation of the formula I, but which becomes evident only on interaction of the three components: antidote/agricultural chemical/plant. Similarly to the action of a pesticidally acting chemical, of which the pesticidal action does not become visible until an insect pest is present, the safener action requires in order to become evident the presence of the other two components which participate in the action, namely the agricultural chemical (for example the herbicide) and the cultivated plant. This behaviour renders a formulated 'safener' composition fundamentally different from a synergistically acting two- or three-component mixture in which all active-substance components are simultaneously present and all act in the same direction.

Various substances have already been suggested as antidotes which are capable of specifically antagonising the harmful action of a herbicide on the cultivated plant, that is to say, of protecting the cultivated plant without noticeably impairing the herbicidal action on the weeds to be controlled. Depending on its properties, an antidote of the said type can be used for pretreating the seed of cultivated plants (dressing of the seed or of the seedlings); or it can be applied into the seed furrows before sowing; or it can be applied as a tank mixture, on its own or together with the herbicide, before or after emergence of the plants.

Thus, the G.B. Patent Specification No. 1,277,557 describes the treatment of seed, or of seedlings, of wheat and sorghum with certain oxamic acid esters and amides before they become attacked by N-methoxymethyl-2',6'-diethyl-chloroacetanilide (Alachlor). According to other references (German Offenlegungsschriften Nos. 1,952,910 and 2,245,471 and French Patent Specification No. 2,021,611), antidotes are suggested for the treatment of the seed of cereals, maize and rice for protection against attack from herbicidal thiocarbamates. In the German Offenlegungschrift No. 1,576,676 and U.S. Pat. No. 3,131,509, there are suggested hydroxy-amino-acetanilides and hydantoins for protecting the seed of cereals against carbamates, such as IPC, CIPC, and so forth. In further development, however, all these preparations have proved inadequate.

Surprisingly, oximes of the formula I have the property of being able to protect cultivated plants from being attacked by agricultural chemicals harmful to such plants, especially herbicides of the widest variety of classes of substances, including 1,3,5-triazines, 1,2,4-triazinones, phenylurea derivatives, carbamates, thiolcarbamates, phenoxyacetic acid esters, phenoxypropionic acid esters, halogenoacetanilides, halogenophenoxyacetic acid esters, subst. phenoxyphenoxyacetic acid esters and -propionic acid esters, subst. pyridineoxyphenoxy-acetic acid esters and -propionic acid esters, benzoic acid derivatives, and the like, in cases where these are not compatible, or insufficiently compatible, with the cultivated crops.

An antidote of the formula I of the said type can be used, depending on the purpose of application, for the pretreatment of the seed of cultivated plants (dressing of the seed or of the seedlings), or it can be applied, before or after sowing, to the soil, or alternatively, on its own or together with the herbicide, before or after emergence of the plants. The treatment of the plants or of the seed with the antidote can therefore be carried out essentially independently of the point of time of application of the phytotoxic chemical. It can however also be carried out simultaneously (tank mixture). The preemergence treatment includes both the treatment of the cultivated area before sowing (ppi="pre plant incorporation") and the treatment of the sown cultivated area before emergence of the plants.

The applied amounts of antidote in proportion to the amount of herbicide depend largely on the type of application. If a field treatment is being undertaken, the amounts of antidote of the formula I in proportion to the phytotoxic chemical are 1:100 to 5:1, preferably 1:20 to 1:1. In the case of seed dressing and similar specific protective measures, there are required much smaller amounts of antidote compared with the amounts of herbicide subsequently used for example per hectare of cultivated area (for example about 1:3000 to 1:1000). As a rule, there is only a loose relationship between protective measures such as seed dressing with an antidote of the formula I and a possible subsequent field treatment with agricultural chemicals. Pretreated seed and plant material can later come into contact with various chemicals in agriculture, horticulture and forestry without suffering damage.

Within the scope of the present invention, cultivated plants are all plants which in some form or other produce productive materials (seeds, roots, stalks, tubers, leaves, blossom, or components such as oils, sugar, starch, protein, and so forth), and which are cultivated for this purpose. These plants include for example: all varieties of cereals, maize, rice, cultivated millet, soybean, beans, peas, potatoes, vegetables, cotton, sugar beet, sugar cane, peanuts, tobacco and hops, and also ornamental plants, fruit trees, as well as banana, cocoa and natural rubber plants. This list does not constitute any limitation. An antidote can essentially be used everywhere where a cultivated plant is to be protected against the phytotoxicity of a chemical.

The invention relates also to a process for protecting cultivated plants against aggressive (phytotoxic) agricultural chemicals, which process comprises applying an oxime derivative of the formula I, which acts as an antidote, either before or after application of the agricultural chemical, or alternatively simultaneously with the agricultural chemical.

The invention relates also to the propagation material of such cultivated plants, which has been protectively treated with an oxime derivative of the formula I. By the term 'propagation material' are meant all generative parts of plants, which can be used for propagating the cultivated plant. These include seeds (seed in the narrower sense), roots, fruits, tubers, rhizomes, parts of stalks, branches (cuttings) and other parts of plants. There are also included however germinated plants and young plants, which are to be transplanted after germination or emergence. Young plants of this kind can be specifically protected by a complete or partial immersion treatment before transplantation.

Compounds of the formula I can be produced from the free oximes by several processes which are illustrated schematically in the following:

The compounds of the formula I are produced by processes known per se (see for example J. F. Prakt. Chemie 66, p. 353; and Liebigs Ann. 250, 165).

By condensation of substituted oximino compounds or salts thereof, particularly alkali metal salts or ammonium salts thereof, with reactive partners, there are formed the compounds of the formula I (Organic Reactions 1953, Vol. 7, pp. 343 and 373).

Depending on the meaning of the substituent Q in the formula I, there are formed oxime ethers, oxime esters, oxime carbamates or oxime carbonates.

The condensation of the substituted oximino compounds with reactive alkyl, alkenyl or alkynyl derivatives is performed in the case of etherification advantageously with the compounds being in the form of their salts, especially their alkali metal salts or ammonium salts, as is shown in the following by selected examples:

oxime ethers of the formula I;

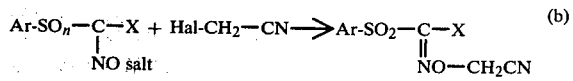

oxime-cyanoalkyl ethers of the formula I;

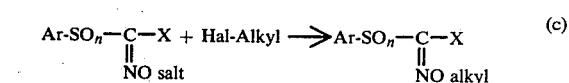

oxime ethers of the formula I;

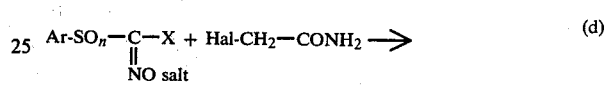

oxime-alkanecarboxylic acid amides of the formula I;

oxime-alkanecarboxylic acid esters of the formula I;

oxime-alkanecarboxylic acid thioesters of the formula I.

The formation of the oxime esters of the formula I is effected advantageously likewise using the oxime salts. It is however also possible to esterify the free oximes, in the presence of acid-binding agents, with suitable acylating agents, as is shown by the following diagrams:

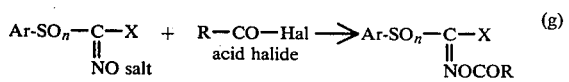

acyl-oxime of the formula I;

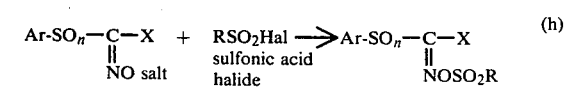

acyl-oxime of the formula I;

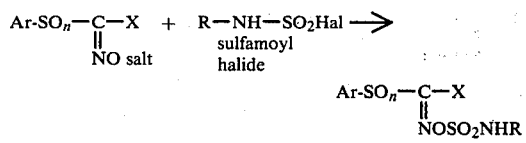 (i)

sulfamoyl-oxime of the formula I.

For producing these esters, the reactive carboxylic halides and carboxylic anhydrides can advantageously be used. Suitable in this process are the reactive derivatives of acetic acid, chloroacetic acids, bromoacetic acids, propionic acids, butyric acids and isobutyric acids, and derivatives of further fatty acids up to cinnamic acid and benzoic acid, as well as their ring-substituted derivatives and further aromatic and heterocyclic carboxylic acids.

The oxime carbamates of the formula I are produced advantageously by reaction of the free oximes with isocyanates, or of the oxime salts with halogenocarbonic acid mono- or disubstituted amides, or with the corresponding halogenothiocarbonic acid amides, as is illustrated by the selected examples given below:

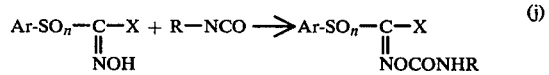 (j)

mono-substituted oxime carbamate of the formula I;

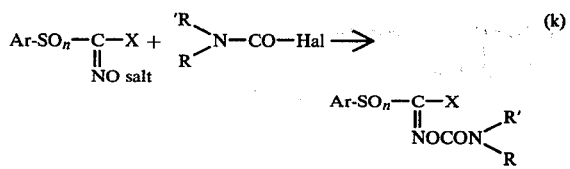 (k)

di-substituted oxime carbamate of the formula I;

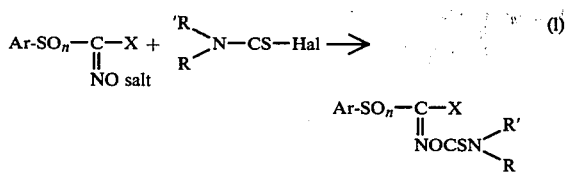 (l)

oxime thiocarbamate of the formula I;

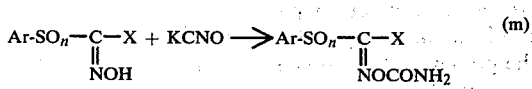 (m)

oxime carbamate of the formula I.

Suitable for producing the carbamates are the carbamic acid halides, more particularly however the isocyanates. The following examples of isocyanates may be mentioned:

| methylisocyanate | trichloromethylisocyanate |
| ethylisocyanate | ethoxymethylisocyanate |
| iso-propylisocyanate | methoxyethylisocyanate |
| t-butylisocyanate | phenylisocyanate |
| n-propylisocyanate | 4-chlorophenylisocyanate |
| sec-butylisocyanate | 2-chlorophenylisocyanate |
| iso-butylisocyanate | 3-chlorophenylisocyanate |
| heptylisocyanate | 2,4-dichlorophenylisocyanate |
| dodecylisocyanate | 2,5-dichlorophenylisocyanate |
| allylisocyanate | 2,6-dichlorophenylisocyanate |
| propargylisocyanate | 3,4-dichlorophenylisocyanate |
| trifluoromethylisocyanate | 3,5-dichlorophenylisocyanate. |
| chloromethylisocyanate | |
| chloroethylisocyanate | |

The aromatic isocyanates can however be substituted differently, for example by bromine, fluorine, iodine, nitro groups, ethoxythioallyl groups, dihalogeno- and trihalogenomethyl groups, for example the trifluoromethyl group, difluoromethyl group, nitrile groups, S—$CF_3$, —O—$CF_3$, formyl groups, sulfonyloxy groups, sulfamides, azidosulfonyl, and so forth. The aromatic isocyanates can be mono- or polysubstituted, identically or differently.

Further suitable isocyanates are tetrahydropropanyl and tetrahydrofuranyl.

Suitable carbamoyl halides which may be mentioned are methylcarbamoyl chloride, dimethylcarbamoyl chloride, methylethylenecarbamoyl chloride, methylmethoxycarbamoyl chloride, methylphenylcarbamoyl chloride and dimethylthiocarbamoyl chloride.

Oxime carbonates of the formula I are produced by reacting oxime salts with halogenocarbonic acid esters or halogenothiocarbonic acid esters. It is also possible to react the free oximes, in the presence of acid-binding agents, with halogenocarbonic acid esters (see the following reaction patterns which illustrate these reactions):

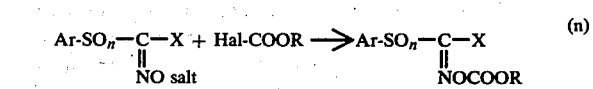 (n)

oxime carbonate of the formula I; and

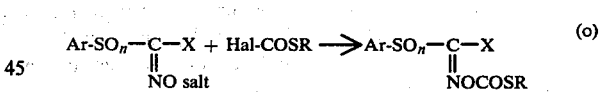 (o)

oximethiocarbamate of the formula I.

Further general reaction possibilities leading to compounds of the formula I are for example: the reactions of oximecarbonic acid halides with amines, alcohols, phenols or mercaptans, wherein oxime carbamates, oxime carbonates or oxime thiocarbonates are formed. These reactions too are illustrated diagramatically in the following:

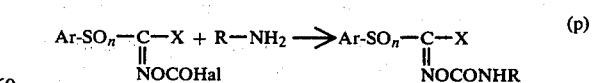 (p)

oxime carbamate of the formula I;

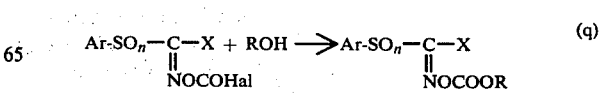 (q)

oxime carbonate of the formula I; and

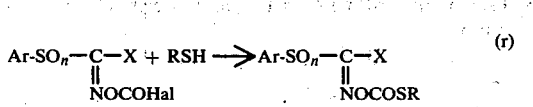

(r)

oxime thiocarbonate of the formula I.

The starting materials, namely the oximes or the salts thereof, required for producing the compounds of the formula I are known (Arch. Pharm. 246, 631). By reaction of the arylsulfonacetonitriles or arylsulfonacetamides, as well as ring-substituted products thereof, with alkylnitriles/Na-ethylate, there are formed the unsubstituted and ring-substituted oximes, respectively, or the sodium salts thereof.

Among the preferred oxime nitriles or oxime acetamides there are the following readily accessible starting products:

The temperatures are within the range of $-20°$ C. to about $150°$ C., preferably between $20°$ and $60°$ C.

As agents splitting off hydrogen halide, it is possible to use bases such as tert. amines (triethylamine, triethylenediamine, N-methylpiperidine, N-methylmorpholine or dimethylaniline).

In some cases, a suspension of anhydrous $Na_2CO_3$ or anhydrous $K_2CO_3$ in an anhydrous reaction medium is sufficient.

Oximes occur in two stereoisomeric forms: the syn. and anti form. All the stated final products correspond to the formula I, and can occur in either form in the pure state or as mixtures. Accordingly, within the scope of the presence specification, there are embraced both stereoisomeric forms separately and as mixtures in any reciprocal mixture ratio.

One of the preferred subgroups of antidotes (or safeners) is formed by compounds of the formula

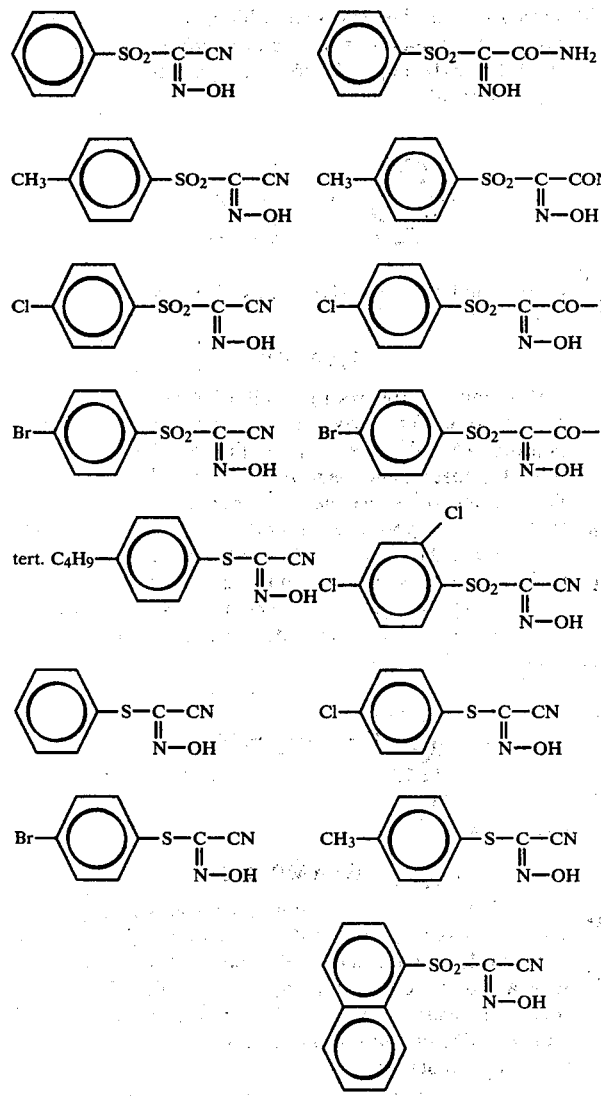

Suitable solvents for obtaining the compounds of the formula I are essentially all representatives which behave inertly under the conditions of the reaction. For example hydrocarbons, especially however polar solvents, such as acetonitrile, dioxane, cellosolve and DMF, and also ketones, such as methyl ethyl ketone.

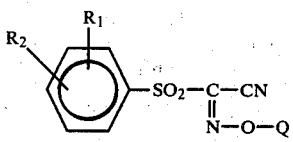

wherein $R_1$ and $R_2$ independently of one another are hydrogen, halogen or $C_1$-$C_4$-alkyl, and Q is hydrogen, a metal cation, the acetamide group, a $C_1$-$C_4$-alkoxycarbonyl group, a $C_1$-$C_4$-alkyl group, a $C_2$-$C_4$-alkenyl group, a $C_1$-$C_4$-alkyl-substituted carbamoyl group or a benzoyl group which is unsubstituted or mono- to tri-substituted by identical or different substituents from the series halogen, $C_1$-$C_4$-alkyl and $C_1$-$C_4$-alkoxy.

Preferred compounds among the compounds of the above subgroup are those of the following formula

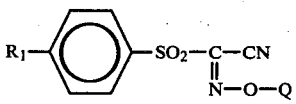

wherein $R_1$ is hydrogen, chlorine, methyl or ethyl, and Q is hydrogen, an alkali metal cation, —$CH_2CONH_2$, —$COOCH_3$, a $C_1$-$C_4$-alkyl group, a $C_2$-$C_4$-alkenyl group, an N-methyl-carbamoyl group, or a benzoyl group which is substituted by two chlorine atoms and a methoxy group.

Important individual compounds within the aforementioned subgroup of antidotes are the compounds Nos. 7, 9, 13, 18, 38, 45, 46, 47, 50 and 51 listed in the Table shown later in the text.

The following Examples illustrate the production of the compounds of the formula I. There is subsequently given a Table of compounds produced in a manner analogous to that described in these Examples. The temperature values are given in degrees Centigrade, and percentages relate to weight.

EXAMPLE 1

1/10 mol of sodium phenylsulfonylglyoxylonitrile-oxime (produced according to Arch. der Pharmazie 246, p. 631) is suspended in acetonitrile, and to the suspension is added the equimolar amount of chloroacetonitrile. The reaction medium is heated for 2 hours at 60°, and the solvent is then distilled off in vacuo in a rotary evaporator. The residue is taken up in methylene chloride and washed with water. The organic layer is is dried with $Na_2SO_4$, and concentrated in vacuo to leave a residue in the form of a crystalline product of the formula

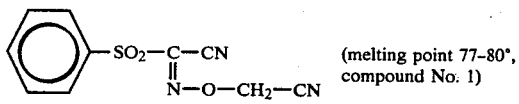

(melting point 77-80°, compound No. 1)

EXAMPLE 2

1/10 mol of sodium 4-bromophenylsulfonylglyoxylonitrile-oxime is finely ground, and suspended in a small amount of anhydrous ether; the calculated amount of freshly distilled benzoyl chloride is then added, and the mixture is heated for a considerable time on a water-bath. The substance which has precipitated is recrystallised from chloroform to yield the product of the formula

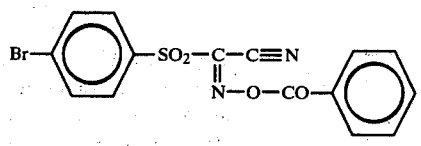

having a melting point of 170°-172° (compound No. 2).

EXAMPLE 3

10 g of sodium 4-methylphenylsulfonyl-glyoxylonitrile-oxime is finely ground, and then suspended in 50 ml of acetonitrile. After the addition of 24.2 g of allyl bromide, the mixture is held for 2 hours at a bath temperature of 50°-60°; it is subsequently concentrated by evaporation, and the semi-solid residue is stirred up with water, in the process of which the product precipitates as a beige-coloured crystalline product; yield 9.7 g (91.5% yield); m.p. 34°-36°. The product corresponds to the formula

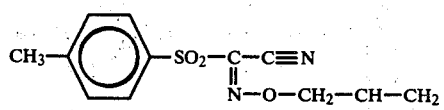

(compound No. 3), and contains 11.6% of sulfur (calculated 12.13%).

EXAMPLE 4

0.04 mol of the sodium salt of 4-methylphenylsulfonylglyoxylonitrile-oxime is finely ground, and suspended in 50 ml of acetonitrile. There is then added 0.04 mol of iodoacetamide, and the mixture is held at 50°-60° for 2 hours, and subsequently concentrated by evaporation at this temperature. Methylene chloride is added to the residue; the mixture is filtered with animal charcoal and concentrated by evaporation; m.p. 115°-122°. Recrystallised from methanol/$H_2O$, the product has a m.p. of 130°-131° and corresponds to the formula

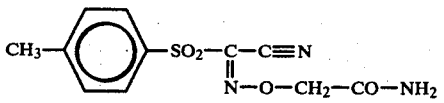

(compound No. 4).

EXAMPLE 5

To 1/10 mol of 4-chlorophenylsulfonylglyoxyloacetamide-oxime, m.p. 155°, in acetonitrile is added excess methylisocyanate, and the mixture is held for several hours at 60°. The reaction mixture is concentrated in vacuo, and the residue is recrystallised from alcohol. The condensation product corresponds to the following formula

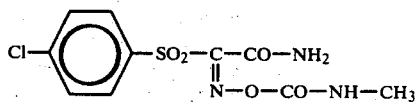

(compound No. 5).

EXAMPLE 6

1/10 mol of sodium phenylthioglyoxylonitrile-oxime with the equimolar amount of chloroacetonitrile in acetonitrile is held for 2 hours at 60°, and is subsequently further processed in the manner described in Example 1. The product is obtained in the form of oil and corresponds to the formula

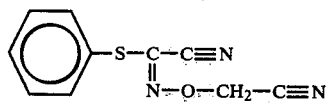

EXAMPLE 7

10 g of phenylsulfonylglyoxylonitrile oxide (0.05 mol) is dissolved in 100 cc of acetonitrile, a spatula tip of DABCO is added followed by 10.8 g of methylisocyanate (0.2 mol). A slight temperature rise from 23° to 27° is observed. The mixture is held for 5 hours at 50°–60°, whereupon a fine suspension is formed. The reaction mixture is stirred into about 500 ml of ice-water, and the product which has precipitated out in a finely crystalline form is filtered off with suction and washed with water. The product obtained melts at 120°–123° and corresponds, by virtue of the process and analysis, to the formula

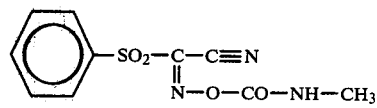

(compound No. 7), the analysis being as follows:

| calculated | found |
|---|---|
| C 44.94% | C 45.4% |
| H 3.39% | H 3.6% |
| N 15.72% | N 15.7% |
| S 12.00% | S 11.9%. |

The compounds listed in the Table which follows are obtained in a manner analogous to that described in the above Examples.

$$Ar-SO_n-\underset{\underset{N-O-Q}{\|}}{C}-X$$

| Comp. No. | Ar | $SO_n$ | Q | X | Physical constants |
|---|---|---|---|---|---|
| 1 | phenyl | $SO_2$ | $CH_2CN$ | CN | m.p. 77–78° |
| 2 | 4-Br-phenyl | $SO_2$ | CO-phenyl | CN | m.p. 170–172° |
| 3 | 4-$CH_3$-phenyl | $SO_2$ | $CH_2-CH=CH_2$ | CN | m.p. 34–36° |
| 4 | 4-$CH_3$-phenyl | $SO_2$ | $CH_2-CONH_2$ | CN | m.p. 130–131° |
| 5 | 4-Cl-phenyl | $SO_2$ | $CONHCH_3$ | $CONH_2$ | — |
| 6 | phenyl | S | $CH_2-CH=CH_2$ | CN | oil |
| 7 | phenyl | $SO_2$ | $CO-NHCH_3$ | CN | m.p. 120–123° |
| 8 | 4-$CH_3O$-phenyl | $SO_2$ | $CH_3$ | CN | m.p. 94° |
| 9 | phenyl | $SO_2$ | CO-(2,6-diCl-3-$CH_3O$-phenyl) | CN | m.p. 109–111° |
| 10 | 4-$CH_3$-phenyl | $SO_2$ | $-CH_2-C\equiv CH$ | CN | m.p. 83° |
| 11 | phenyl | $SO_2$ | CO-(thienyl) | CN | m.p. 155–156° |
| 12 | phenyl | $SO_2$ | $COCH_2OCH_3$ | CN | m.p. 60–62° |
| 13 | phenyl | $SO_2$ | $CH_2CONH_2$ | CN | m.p. 129–130° |
| 14 | 4-$CH_3$-phenyl | $SO_2$ | $CH_2CN$ | CN | resin |
| 15 | 4-Cl-phenyl | $SO_2$ | $CON(CH_3)_2$ | CN | m.p. 111–114° |

-continued $$Ar-SO_n-\underset{\underset{N-O-Q}{\parallel}}{C}-X$$

| Comp. No. | Ar | $SO_n$ | Q | X | Physical constants |
|---|---|---|---|---|---|
| 16 | CH$_3$—◯— | SO$_2$ | CONHCH$_3$ | CN | m.p. 100–104° |
| 17 | Cl—◯— | SO$_2$ | CONHCH$_3$ | CN | m.p. 125–128° |
| 18 | Cl—◯— | SO$_2$ | COOCH$_3$ | CN | m.p. 114–116° |
| 19 | CH$_3$—◯— | SO$_2$ | CH(CH$_3$)COOCH$_3$ | CN | m.p. 90–91° |
| 20 | CH$_3$—◯— | SO$_2$ | CH$_2$—CHBr=CH$_2$ | CN | m.p. 29–30° |
| 21 | CH$_3$—◯— | SO$_2$ | ⟨H⟩ | CN | m.p. 60–63° |
| 22 | CH$_3$—◯— | SO$_2$ | CH$_2$—S—CH$_3$ | CN | m.p. 38–41° |
| 23 | Cl—◯— | SO$_2$ | —CH$_2$—C≡CH | CN | m.p. 86° |
| 24 | CH$_3$—◯— | SO$_2$ | CH$_2$COOC$_2$H$_5$ | CN | m.p. 61° |
| 25 | ◯ | SO$_2$ | CON(CH$_3$)$_2$ | CN | |
| 26 | ◯ | S | CH$_2$CONH$_2$ | CN | |
| 27 | ◯ | SO$_2$ | CH$_2$COOiC$_3$H$_7$ | CN | |
| 28 | ◯ | SO$_2$ | CH$_2$COOH | CN | |
| 29 | CH$_3$—◯— | SO$_2$ | SO$_2$CH$_3$ | CN | |
| 30 | ◯ (CF$_3$) | SO$_2$ | CONHCH$_3$ | CN | |
| 31 | NO$_2$—◯— | SO$_2$ | CONHCH$_3$ | CN | |
| 32 | F—◯— | SO$_2$ | CH$_2$CN | CN | |
| 33 | F—◯— | SO$_2$ | CH$_2$CN | CONH$_2$ | |
| 34 | Cl—◯— | SO$_2$ | CO—◯ | CN | |
| 35 | Br—◯— | SO$_2$ | CO—◯ | CN | |
| 36 | I—◯— | SO$_2$ | CO—◯ | CN | |
| 37 | CH$_3$—◯— | SO$_2$ | CH$_3$ | CN | solid |
| 38 | Cl—◯— | SO$_2$ | CH$_3$ | CN | m.p. 110° |
| 39 | Br—◯— | SO$_2$ | CH$_3$ | CN | |
| 40 | I—◯— | SO$_2$ | CH$_3$ | CN | |

-continued $$\text{Ar}-\text{SO}_n-\underset{\underset{\text{N}-\text{O}-\text{Q}}{\|}}{\text{C}}-\text{X}$$

| Comp. No. | Ar | $SO_n$ | Q | X | Physical constants |
|---|---|---|---|---|---|
| 41 | CH$_3$O—〇— | SO$_2$ | CH$_3$ | CN | |
| 42 | C$_2$H$_5$O—〇— | SO$_2$ | CH$_3$ | CN | |
| 43 | CH$_3$—〇— | SO$_2$ | O$_n$C$_3$H$_7$ | CN | oil |
| 44 | CH$_3$—〇— | SO$_2$ | H | CN | |
| 45 | Cl—〇— | SO$_2$ | H | CN | solid |
| 46 | CH$_3$—〇— | SO$_2$ | Na$^\oplus$ | CN | solid |
| 47 | CH$_3$—〇— | SO$_2$ | CH$_2$CONH$_2$ | CN | m.p. 130–132 |
| 48 | Cl—〇— | SO$_2$ | CH$_2$CN | CN | $n_D^{20}$ 1.5472 |
| 49 | Cl—〇— | SO$_2$ | CH$_2$CONH$_2$ | CN | m.p. 148° (decomp.) |
| 50 | 〇— | SO$_2$ | CH$_2$CH=CH—CH$_3$ | CN | oil |
| 51 | 〇— | SO$_2$ | CO—furyl | CN | m.p. 150–2° |
| 52 | 〇— | SO$_2$ | SO$_2$N(CH$_3$)$_2$ | CN | $n_D^{20}$ 1.5347 |
| 53 | CH$_3$—〇— | SO$_2$ | SO$_2$N(CH$_3$)$_2$ | CN | $n_D^{20}$ 1.5383 |
| 54 | Cl—〇— | SO$_2$ | SO$_2$N(CH$_3$)$_2$ | CN | $n_D^{20}$ 1.5330 |
| 55 | CH$_3$—〇— | SO$_2$ | —CH$_2$CH=CH—CH$_3$ | CN | oil |
| 56 | 〇— | SO$_2$ | Na$^\oplus$ | CN | solid |
| 57 | Cl—〇— | SO$_2$ | n-C$_3$H$_7$ | CN | m.p. 67–68° |

The antagonistic action against strong herbicides harmful to cultivated plants was verified by the following tests.

Pre-emergence antidote test (basic test)

General procedure

Small flower pots (upper diam. 6 cm) are filled with garden soil, into which the cultivated plant is sown, covered and lightly pressed down. The substance to be tested as antidote is then sprayed on in the form of a dilute solution (obtained from a wettable powder) in an amount equivalent to 4 kg of active substance per hectare. The herbicide is sprayed on directly afterwards in a corresponding manner. After 18 days' standing at about 20°–23° with 60–70% relative humidity, an evaluation is made on the basis of a linear scale of ratings from 1 to 9, with the rating 1 denoting total destruction of the plant and the rating 9 denoting unimpaired condition of health of the plant. Plants without antidote protection are used as a control.

The following are used:

(1) 1.5 kg of active substance per hectare (AS/hect.) of α-[4-(p-trifluoromethylphenoxy)-phenoxy]-propionic acid-n-butoxyethyl ester in maize of the "Orla 264" variety;

(2) 1.5 kg of AS/hect. of Metolachlor = N-(1-methyl-2-methoxyethyl)-N-chloroacetyl-2-ethyl-6-methylaniline in sorghum-millet of the "Funk G-522" variety;

(3) 2.0 kg of AS/hect. of Prometryn = 2,4-bis-(isopropylamino)-6-methylthio-s-triazine in soya-bean;

(4) 2.0 kg of AS/hect. of 4-ethylamino-6-tert-butylamino-2-chloro-s-triazine in wheat of the "Farnese" variety;

(5) 4.0 kg of AS/hect. of Prometryn = 2,4-bis-(isopropylamino)-6-methylthio-s-triazine in sorghum millet of the "Funk G-522" variety; and (6) 2.0 kg of AS/hect. of α-[4-(p-trifluoromethyl-phenoxy)phenoxy]-propionic acid-n-butoxyethyl ester in barley of of the "Mazurka" variety.

The following results are obtained with the compounds of the formula I:

| Test variant | Comp. No. | Rating of the herbicidal action (without/with antidote) | |
|---|---|---|---|
| 1 | 38 | 1 | 3 |
| 5 | 18 | 6 | 8 |
| 5 | 47 | 6 | 8 |
| 6 | 45 | 4 | 6 |
| 6 | 46 | 4 | 8 |
| 3 | 50 | 3 | 5 |

Pre-emergence antidote test in nutrient solution (rice)

A Hewitt nutrient solution is prepared containing additionally 10 ppm of the antidote to be tested.

Rice seeds of the "IR-8" variety are sown in an inert filler material (granulated Zonolite) which is contained in a plastic flower pot (upper diam. 6 cm) having a pierced bottom. This pot is placed into a second transparent plastic flower pot (upper diam. 7 cm), in which there is about 50 ml of the prepared nutrient solution; this solution then rises by capillary attraction in the filler material of the smaller pot and wets the seeds and germinating plants. The loss of liquid is made up daily with pure Hewitt nutrient solution to 50 ml. After 15 days, the rice plants in the 2- to 2½-leaf stage are transplanted into rectangular plastic pots (8×8 cm, 10 cm in height), which are filled with 500 ml of boggy-wet soil. The water level on the next day is raised therein to 1–2 cm above the level of the soil. Four days after transplanting, there is added to the water the herbicide 2-ethylamino-4-(1,2-dimethyl-n-propylamino)-6-methylthio-s-triazine in granular form and in an amount which, when converted, corresponds to 0.75 kg of AS/hectare. Three weeks after the addition of the herbicide, an evaluation is made according to a linear scale from 1 to 9, the rating 1 signifying total plant destruction, and the rating 9 an unimpaired condition of health of the cultivated plants. The control solution used in a parallel test contains no antidote.

The compounds of the formula I result in the phytotoxic action of the triazine herbicide being clearly reduced to the extent shown in the following Table.

| Comp. No. | Rating of the herbicidal action (without/with antidote) | |
|---|---|---|
| 38 | 1 | 6 |
| 23 | 1 | 4 |
| 3 | 1 | 4 |

Pre-emergence antidote test in nutrient solution

There is prepared a Hewitt solution containing the amount of herbicide given in the following and also 10 ppm of the antidote to be tested.

The seed used is cultivated seed which could be expected to suffer damage from the employed herbicide at the given test concentration, and the seed is sown in granulated Zonolite (=expanded vermiculite) which is contained in a plastic flower pot having a pierced bottom (upper diam. 6 cm). This pot is placed into a second transparent plastic flower pot (upper diam. 7 cm), in which there is about 50 ml of the nutrient solution that has been prepared with herbicide and antidote; this solution then rises by capillary attraction in the filler material of the smaller pot and wets the seeds and germinating plants. The loss of liquid is made up daily with pure Hewitt nutrient solution to 50 ml. Three weeks after commencement of the test, an evaluation is made on the basis of a linear scale from 1 to 9, the rating 1 signifying total plant destruction, and the rating 9 signifying an unimpaired condition of health in the cultivated plants. The control solution used in a parallel test contains no antidote addition.

There are used the following:

(1) 4 ppm of Prometryn=2,4-bis-(isopropylamino)-6-methylthio-s-triazine in *sorghum-millet* of the "Funk G-522" variety;

(2) 4 ppm of 4-ethylamino-6-tert-butylamino-2-chloro-s-triazine in *wheat* of the "Farnese" variety;

(3) 4 ppm of α-[4-(p-trifluoromethylphenoxy)-phenoxy]propionic acid-n-butoxyethyl ester in *barley* of the "Mazurka" variety; and (4) 5 ppm of Metolachlor=N-(1-methyl-2-methoxyethyl)-N-chloroacetyl-2-ethyl-6-methylaniline in *sorghum-millet* of the "Funk G-522" variety.

The following results are obtained with the compounds of the formula I:

| Test variant | Comp. No. | Rating of the herbicidal action (without/with antidote) | |
|---|---|---|---|
| 3 | 10 | 2 | 4 |
| 4 | 50 | 4 | 6 |
| 4 | 51 | 4 | 7 |

Antidote test with seed soaking

Rice seeds of the IR 8 variety are saturated during 48 hours with solutions of the test substances of 10 and 100 ppm concentration, respectively. The seeds are subsequently allowed to dry for about 2 hours, until they no longer stick together. Rectangular plastic pots (8×8 cm, 10 cm in height) are filled to within 2 cm of the upper edge with sandy loam. In each pot is sown 4 g of seed, and the seed is only very slightly covered (about the diameter of a seed). The soil is maintained in a moist (not boggy) condition. There is then applied the herbicide N-(1-methyl-2-methoxyethyl)-N-chloroacetyl-2-ethyl-6-methylaniline in dilute solution and in an amount which, when converted, is equivalent to 1.5 kg of AS/hectare. After 7 and 18 days, respectively, after planting, an evaluation is made according to a linear scale from 1 to 9, the rating 1 signifying total destruction of the plants, and the rating 9 signifying an unimpaired condition of health of the cultivated plants.

As is seen from the following Table, compounds of the formula I were able in this test to protect the rice seedlings against the phytotoxic action of the herbicide employed.

| Comp. No. | Concentration | Rating of the herbicidal action (without/with antidote) | |
|---|---|---|---|
| 45 | 10 ppm | 2 | 6 |
| 9 | 100 ppm | 3 | 6 |
|  | 10 ppm | 3 | 6 |
| 50 | 100 ppm | 3 | 6 |
|  | 10 ppm | 3 | 7 |

-continued

| Comp. No. | Concentration | Rating of the herbicidal action (without/with antidote) | |
|---|---|---|---|
| 55 | 10 ppm | 3 | 5 |
| 11 | 10 ppm | 3 | 5 |
| 51 | 10 ppm | 3 | 6 |

Post-emergence antidote test in nutrient solution

General procedure

Plastic flower pots (upper diameter 6 cm), which have a pierced bottom, are filled with granulated Zonolite and the cultivated seeds are sown therein. The pot is then placed into a second transparent plastic flower pot (upper diam. 7 cm) in which there is 50 ml of water; this water rises by capillary attraction and wets the seeds. From the fifth day the continuous loss of water is made up with Hewitt nutrient solution. From the fifteenth day, when the cultivated plants are in the 1½- to 2-leaf stage, there is added to the nutrient solution, made up again to 50 ml, 10 ppm of the antidote to be tested + the amount of herbicide given below.

From the sixteenth day, the loss of liquid is again made up with pure Hewitt nutrient solution. During the entire duration of the test, the temperature is 20°-23° with a relative humidity of 60-70%. Three weeks after addition of the herbicide and antidote, an evaluation is made on the basis of a linear scale from 1 to 9, the rating 1 signifying total destruction of the plants, and the rating 9 signifying an unimpaired condition of health of the cultivated plants.

Test variants (1) 8 ppm of α-[4-(3,5-dichloropyridyl-2-oxy)-phenoxy]propionic acid propargyl thiol ester in *wheat* of the "Zenith" variety;

(2) 4 ppm of 4-ethylamino-6-tert-butylamino-2-chloro-s-triazine in *wheat* of the "Zenith" variety;

(3) 2 ppm of α-[4-(p-trifluoromethylphenoxy)-phenoxy]propionic acid-n-butoxyethyl ester in maize of the "Orla" variety;

(4) 8 ppm of α-[4-(p-trifluoromethylphenoxy)-phenoxy]propionic acid-n-butoxyethyl ester in *sorghum-millet* of the "Funk G-522" variety; and (5) 4 ppm of Prometryn=2,4-bis-(isopropylamino)-6-methylthio-s-triazine in *sorghum-millet* of the "Funk G-522" variety.

Compounds of the formula I exhibited in these tests the following antidote action:

| Test variant | Comp. No. | Rating of the herbicidal action (without/with antidote) | |
|---|---|---|---|
| 1 | 13 | 4 | 7 |
| 1 | 37 | 4 | 7 |
| 3 | 43 | 3 | 6 |
| 5 | 46 | 1 | 4 |

Antidote action in the case of separate application (antidote-pre-emergence: herbicide-post-emergence)

General procedure

Small flower pots (upper diam. 6 cm) are filled with sandy loam, into which the cultivated plants are sown. After the seeds have been covered, the substance to be tested is sprayed in dilute solution, onto the surface, in an amount corresponding, when converted, to 4 kg of AS/hectare. The temperature is kept at 20°-23° and the relative humidity to 60-70%. When the plants after 10 days have reached the 2- to 3-leaf stage, they are treated, as given in the following, with the corresponding amount of herbicide. Fourteen days after application of the herbicide, an evaluation is made according to a linear scale from 1 to 9, the rating 1 signifying total destruction of the plants and the rating 9 signifying an unimpaired condition of health of the cultivated plants.

There are used:

(1) 4.0 kg of AS/hectare of Ametryn=2-ethylamino-4-isopropylamino-6-methylthio-s-triazine in *maize* of the "Orla 264" variety;

(2) 1.0 kg of AS/hectare of Prometryn=2,4-bis-(isopropylamino)-6-methylthio-s-triazine in *sorghum-millet* of the "Funk G-522" variety; and (3) 0.25 kg of AS/hectare of α-[4-(p-trifluoromethylphenoxy)phenoxy)]-propionic acid-n-butoxyethyl ester in *barley* of the "Mazurka" variety.

| Test variant | Comp. No. | Rating of the herbicidal action (without/with antidote) | |
|---|---|---|---|
| 2 | 47 | 3 | 5 |
| 2 | 18 | 3 | 5 |
| 2 | 51 | 3 | 7 |
| 2 | 11 | 3 | 7 |
| 2 | 52 | 3 | 8 |
| 2 | 58 | 3 | 6 |
| 3 | 45 | 4 | 6 |
| 3 | 46 | 4 | 8 |
| 3 | 55 | 4 | 6 |

Antidote action on transplanted rice with separate application (antidote pre-emergence + herbicidal post-emergence)

Plastic pots (8×8×10 cm in height) are filled to within 2 cm of the upper edge with soil in the boggy-wet condition. The substance to be tested as antidote is sprayed in dilute solution, onto the surface, in an amount corresponding to 4 kg of AS/hectare. Rice plants of the "IR-8" variety in the 1½- to 2-leaf stage are transplanted into the pots prepared in the said manner. The water level is raised to about 1.5 cm on the next day. Four days after transplanting, there is added to the water 2-ethylamino-4-(1,2-dimethyl-n-propylamio)-6-methylthio-s-triazine in granular form in an amount which, when converted, corresponds to 0.75 kg of AS/hectare. The temperature during the test is 26°-28°, and the relative humidity is 60-80%. Twenty days after treatment with the herbicide, an evaluation is made according to a linear scale from 1 to 9, the rating 1 signifying total destruction of the plants and the rating 9 signifying an unimpaired condition of health of the plants. Plants without antidote protection are used in control tests.

The following results are obtained with the compounds of the formula I:

| Comp. No. | Rating of the herbicidal action (without/with antidote) | |
|---|---|---|
| 47 | 3 | 9 |
| 18 | 3 | 7 |
| 57 | 3 | 6 |

| Comp. No. | Rating of the herbicidal action (without/with antidote) | |
| --- | --- | --- |
| 7 | 3 | 6 |
| 56 | 3 | 6 |
| 49 | 3 | 6 |
| 50 | 3 | 6 |
| 53 | 3 | 6 |

The compounds of the formula I can be used on their own or together with the active substances to be antagonised, and also together with suitable carriers and/or other additives. Suitable carriers and additives can be solid or liquid and they correspond to the substances common in formulation practice, such as natural or regenerated mineral substances, solvents, dispersing agents, wetting agents, adhesives, thickeners, binders and/or fertilisers.

The content of active substance in commercial compositions is between 0.01 and 90%.

For application, the compounds of the formula I can be in the following forms (the weight-percentage figures in brackets signify advantageous amounts of active substance):

Solid Preparations: dusts and scattering agents (up to 10%), granulates [coated, impregnated or homogeneous granules] and pellets (1 to 80%);

Liquid Preparations:
(a) water-dispersible concentrates of active substance: wettable powders and pastes (25 to 90% in the commercial packing, 0.01 to 15% in ready-for-use solutions); emulsion concentrates and solution concentrates 10 to 50%, 0.01 to 15% in ready-for-use solutions);
(b) solutions (0.1 to 20%), for example for dressing, aerosols.

The active substances of the formula I of the present invention can be formulated for example as follows:

Dusts

The following substances are used to produce (a) a 5% dust and (b) a 2% dust:

(a)
5 parts of active substance,
95 parts of talcum; and (b)
2 parts of active substance,
1 part of highly dispersed silicic acid, and
97 parts of talcum.

The active substance is mixed and ground with the carriers, and in this form can be applied by dusting.

Granulate

The following ingredients are used to produce a 5% granulate:
5 parts of active substance,
0.25 part of epichlorohydrin,
0.25 part of cetyl polyglycol ether,
3.50 parts of polyethylene glycol, and
91 parts of kaolin (particle size 0.3–0.8 mm).

The active substance is mixed with epichlorohydrin and the mixture is dissolved in 6 parts of acetone; the polyethylene glycol and cetyl polyglycol ether are then added. The solution thus obtained is sprayed onto kaolin and the acetone is subsequently evaporated off in vacuo. A microgranulate of this type can be advantageously worked into seed furrows.

Wettable powder

The following constituents are used to produce a 70% wettable powder:
70 parts of active substance,
5 parts of sodium dibutyl-naphthyl sulfonate,
3 parts of a naphthalenesulfonic acid/phenolsulfonic acid/formaldehyde condensate 3:2:1,
10 parts of kaolin, and
12 parts of Champagne chalk.

The active substances are intimately mixed in suitable mixers with the additives, and the mixture is then ground in the appropriate mills and rollers. There are obtained wettable powders which have excellent wetting and suspension properties, which can be diluted with water to give suspensions of the desired concentration, and which can be used in particular for seed dressing and for the immersion treatment of seedlings.

Emulsifiable concentrate

The following substances are used to produce a 25% emulsifiable concentrate:
25 parts of active substance,
2.5 parts of epoxidised vegetable oil,
10 parts of an alkylarylsulfonate/fatty alcohol polyglycol ether mixture,
5 parts of dimethylformamide, and
57.5 parts of xylene.

Emulsions of the required concentration can be prepared from a concentrate of this type by dilution with water, and these emulsions are particularly suitable for seed dressing and for the immersion treatment of young plants.

What is claimed is:

1. A compound of the formula

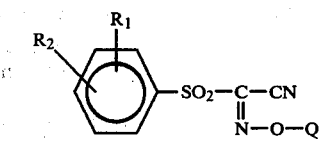

wherein $R_1$ and $R_2$ independently of one another are each hydrogen, halogen or $C_1$–$C_4$-alkyl, and Q is acetamide or a $C_1$–$C_4$-alkyl-substituted carbamoyl group.

2. A compound of the formula

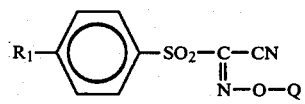

wherein $R_1$ is hydrogen, chlorine, methyl or ethyl, and Q is —$CH_2CONH_2$ or an N-methylcarbamoyl group.

3. A compound of the formula

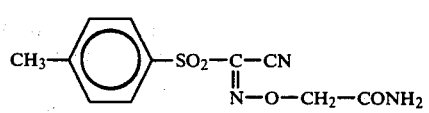

according to claim 2.

4. A comound of the formula

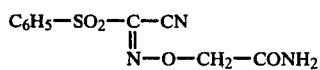
according to claim 2.
5. A compound of the formula
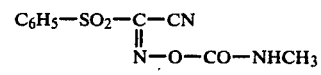
according to claim 2.
6. A compound of the formula
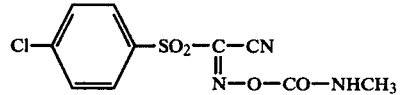
according to claim 2.
* * * * *